(12) United States Patent
Nobuto et al.

(10) Patent No.: US 7,507,261 B2
(45) Date of Patent: Mar. 24, 2009

(54) HAIR DYE COMPOSITION

(75) Inventors: Yuko Nobuto, Sumida-ku (JP); Masayoshi Nojiri, Sumida-ku (JP)

(73) Assignee: Kao Corporation, Tokyo (JP)

( * ) Notice: Subject to any disclaimer, the term of this patent is extended or adjusted under 35 U.S.C. 154(b) by 133 days.

(21) Appl. No.: 11/616,469

(22) Filed: Dec. 27, 2006

(65) Prior Publication Data
US 2007/0157399 A1    Jul. 12, 2007

(30) Foreign Application Priority Data

| Dec. 28, 2005 | (JP) | ............................. 2005-377208 |
| Dec. 28, 2005 | (JP) | ............................. 2005-377209 |
| Sep. 29, 2006 | (JP) | ............................. 2006-267046 |

(51) Int. Cl.
*A61Q 5/10* (2006.01)

(52) U.S. Cl. ....................... 8/405; 8/406; 8/435; 8/581; 8/587; 8/606; 8/107; 8/110

(58) Field of Classification Search ..................... 8/405, 8/406, 435, 581, 587, 606, 107, 110
See application file for complete search history.

(56) References Cited

U.S. PATENT DOCUMENTS

| 4,362,528 | A |    | 12/1982 | Grollier et al. |
| 4,752,467 | A |    | 6/1988 | Konrad et al. |
| 5,843,193 | A |    | 12/1998 | Hawkins et al. |
| 6,540,791 | B1 | * | 4/2003 | Dias ............................. 8/111 |

FOREIGN PATENT DOCUMENTS

| EP | 0 780 117 A1 | 6/1997 |
| EP | 0 928 608 A2 | 7/1999 |
| JP | 63-51315 | 3/1988 |
| JP | 8-217651 | 8/1996 |
| JP | 2005-255534 | 9/2005 |
| WO | WO 99/36047 | 7/1999 |
| WO | WO 02/087526 A1 | 11/2002 |

OTHER PUBLICATIONS

STIC Search Report dated Jul. 8, 2008.*

Akio Yonetani, et al., "Acidic hair dye compositions containing aromatic alcohols and trimethylglycine", Database CA [Online] Chemical Abstracts Service, Columbus, Ohio, US; XP002432591, Nov. 8, 1996, 1 Page.

Derwent Publications Ltd., London, GB: AN 1996-439450, Database WPI Week 199644, XP002432649, 1 Page.

L. Rigano, et al., "Benefits of trimethylglycine (Betaine) in personal-care formulations", Cosmetics and Toiletries, Wheaton, IL US, vol. 115, No. 12, XP002954567, Dec. 2000, pp. 47-53.

* cited by examiner

*Primary Examiner*—Eisa B Elhilo
(74) *Attorney, Agent, or Firm*—Oblon, Spivak, McClelland, Maier & Neustadt, P.C.

(57) ABSTRACT

A hair dye composition which is provided by mixing a first-part agent containing an alkaline agent and a second-part agent containing an oxidizing agent upon application, comprising, after mixing, components (a) to (c) and an oxidative dye (d) as needed, wherein the pH after mixing is 8 to 12 and the content of component (a) is 0.1 to 20 wt. %:

(a) a betaine compound represented by formula (1) and an acid-addition salt thereof:

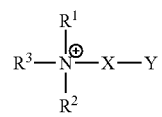

(1)

wherein $R^1$, $R^2$, $R^3$, X, and Y are as defined;

(b) an oxidizing agent; and (c) an ammonia or a salt thereof, which hair dye composition: suppresses the stripping of ammonia at the time of mixing a first-part agent and a second-part agent, thereby reducing the unpleasant odor of ammonia upon application; suppresses hair damage and deterioration of feeling without a pre-treatment; has excellent dying and bleaching effects; and uniformly dyes (bleaches) the hair from the root to the tip of the hair regardless of the degree of hair damage.

20 Claims, No Drawings

HAIR DYE COMPOSITION

FIELD OF THE INVENTION

The present invention relates to a hair dye composition which is provided by mixing a first-part agent containing an alkaline agent and a second-part agent containing an oxidizing agent upon application. The hair dye includes a so-called hair bleaching composition which does not contain an oxidation dye intermediate in a first-part agent, and a so-called hair coloring composition which contains an oxidation dye intermediate.

BACKGROUND OF THE INVENTION

For dying the hair, a hair dye which utilizes an oxidative coupling reaction of an oxidation dye intermediate (i.e., a precursor and a coupler) under the coexistence of an alkaline agent and an oxidizing agent is widely used.

For the alkaline agent, ammonia is often utilized; however, the odor of ammonia becomes a problem. Although a number of solutions have been proposed for reducing the odor of ammonia, the reduction of the odor without impairing bleaching effect thereof is difficult.

It should also be noted that a hair dye containing an oxidizing agent often causes damage to the hair. As a consequence, not only lift-up or flake-away of the cuticle, production of cysteic acid and a reduction in the lipid inside the hair will result but a feeling and appearance of the dyed hair tend to get easily impaired. The impairment to the feeling and appearance is exemplified by a feeling that fingers do not run through the hair smoothly; a feeling of friction; and a rough feeling and so on when the hair is shampooed or dried, and also by deterioration of a hair color/sheen and manageability. Further, such damage to the hair and impairment to the feeling and appearance accumulates as hair dying and bleaching are repeated, which eventually creates an inequality in the degree of damage between the root and the tip of the hair. This causes problems such that unevenness is more likely to be resulted in hair dying, or colors on the hair tip are more easily to fade away by shampooing, etc.

As one method for resolving hair damage and impairment to the feeling and appearance, use of an additive having a conditioning effect has been practiced. For example, addition of a silicone derivative such as a certain kind of amino-modified polysiloxane to an oxidation hair dye (JP-A-S63-51315), and addition of a cationic polymer (U.S. Pat. No. 4,362,528) have been proposed. However, conditioning components as described above are still unsatisfactory due to a drawback that they end up reducing dyeing and bleaching effects when incorporated in an amount necessary to bring about a sufficient conditioning effect.

Alternatively, another method is proposed, in which a "pre-treatment agent" containing trimethylglycine is used before dying the hair to thereby improve the dying effect, which further suppresses hair damage whereby a conditioning effect is provided (JP-A-2005-255534). However, the application procedure disclosed in the Example (i.e., subsequent to application of a pre-treatment agent to the hair, a hair dye is applied without washing) may possibly reduce the dying effect because the concentration of the dye which actually works on the hair is diluted due to the pre-treatment agent applied. Furthermore, a drawback is accompanied such that the operation becomes complicated since application requires a two-step process.

SUMMARY OF THE INVENTION

The present invention provides a hair dye composition which is provided by mixing a first-part agent containing an alkaline agent and a second-part agent containing an oxidizing agent upon application, which contains, after mixing, components (a) to (c) and an oxidation dye (d) as needed; wherein the pH after mixing is 8 to 12 and the content of component (a) is 0.1 to 20 wt. %:

(a) a betaine compound represented by formula (1) and an acid-addition salt thereof:

(wherein $R^1$, $R^2$ and $R^3$ are the same or different from one another and each represents a $C_{1-3}$ alkyl group; X represents a $C_{1-3}$ alkylene group; Y represents $CO_2^-$, $SO_3^-$, $OSO_3^-$ and $OPO_3^-$.);

(b) an oxidizing agent; and (c) an ammonia or a salt thereof.

The present invention further provides a method for dying hair, including mixing a first-part agent and a second-part agent described above right before use; and applying to the hair; and washing it off after letting it stand for a predetermined time.

DETAILED DESCRIPTION OF THE INVENTION

The present invention relates to a hair dye which reduces the odor of ammonia upon application; suppresses hair damage and a deterioration of feeling such as a feeling of friction and a rough feeling and such feeling that fingers do not run through the hair smoothly, etc by an ordinary application procedure without requiring a special pre-treatment agent or the like; has excellent dying and bleaching effects; uniformly dyes (bleaches) the hair from the root to the tip regardless of the degree of hair damage; and a method for dying the hair using the hair dye.

In the present invention, a "hair dye composition" includes a hair bleaching agent which does not contain a dye stuff in addition to a hair dye agent containing a dye stuff. Further, "to dye" refers to dye hair concomitantly with bleaching the hair when a hair dye agent containing a dye stuff is used; and to bleach the hair when a bleaching agent which does not contain a dye stuff is used.

The hair dye of the present invention can be provided as a two-part type composition having a first-part agent containing an alkaline agent and a second-part agent containing an oxidizing agent such as a hydrogen peroxide; or a three-part type composition having a third-part agent in combination, which is a powdery oxidizing agent containing a granulated substance such as persulfate (e.g., ammonium persulfate, potassium persulfate and sodium persulfate) for improving the bleaching effect. Hereinafter a "total composition" in the present invention refers to the whole of the composition right before use in which a first-part agent and a second-part agent have been mixed in a case of a two-part type composition, and the whole of the composition right before use in which a first-part agent, a second-part agent and a third-part agent have been mixed in a case of a three-part type composition.

The hair dye composition of the present invention preferably has a pH of 8-12 at 25° C. at the time of application (i.e., at the time of mixing); however, it preferably has a pH of 9-11 in view of hair dying and bleaching effects as well as skin irritation. Further, a first-part agent preferably has a pH of 8-12 before mixing, and a second-part agent preferably has a pH of 2-5 before mixing. As a pH regulator, an inorganic acid such as hydrochloric acid and phosphoric acid, an organic acid such as citric acid, glycolic acid and lactic acid, hydrochloride such as monoethanolamine hydrochloride, phosphate such as potassium dihydrogen phosphate, disodium hydrogen phosphate can be used in addition to alkaline agents described below.

In the present invention, component (a), i.e., a betaine compound and an acid addition salt thereof, is contained in either one or both of a first-part agent and a second-part agent. The betaine compound of component (a) is a compound in which an amphoteric ion is formed by intramolecular salt, i.e., between a quaternary ammonium cation group and a carboxy anion group, sulfoanion group, sulfuric acid anion group or phosphoric acid anion group. An acid-addition salt of the betaine compound is an addition salt of a physiologically acceptable organic acid or an inorganic acid, and it is preferably a hydrochloric acid, sulfuric acid or phosphoric acid as an inorganic acid; and tartaric acid, malic acid, benzoic acid or salicylic acid as an organic acid. It is more preferably a hydrochloric acid, sulfuric acid or phosphoric acid.

The betaine compound represented by formula (1) or an acid-addition salt thereof is preferably a betaine compound having a structure represented by the below-described formula (2) to (19) or an acid-addition salt thereof, and it is more preferably a glycine betaine represented by formula (2).

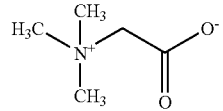

(2)

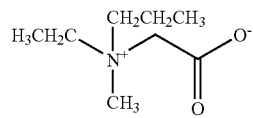

(3)

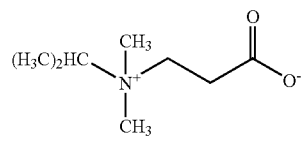

(4)

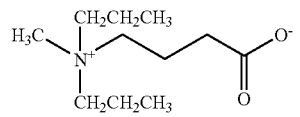

(5)

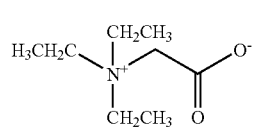

(6)

-continued

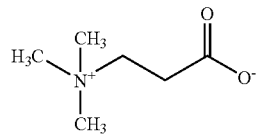

(7)

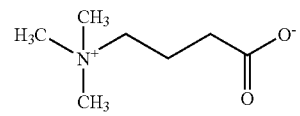

(8)

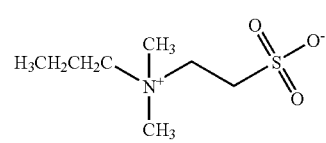

(9)

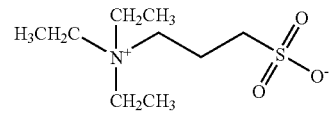

(10)

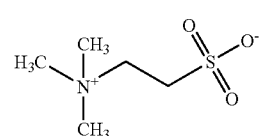

(11)

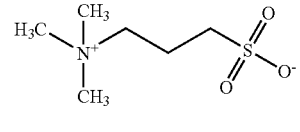

(12)

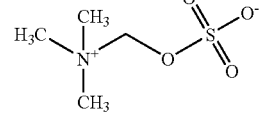

(13)

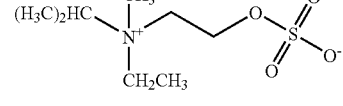

(14)

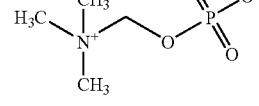

(15)

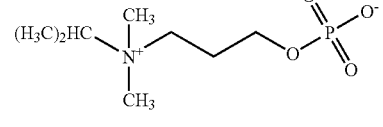

(16)

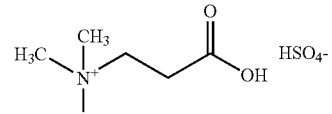

(17)

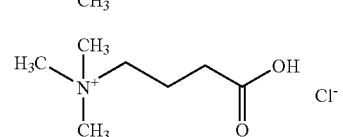

(18)

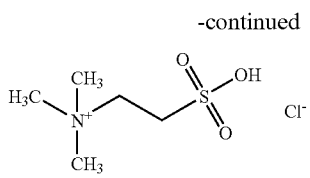

(19)

The content of component (a) is preferably 0.01-20 wt. %, more preferably 0.05-5 wt. % in the total composition in view of the feeling and stability of the composition.

It is preferable that an oxidizing agent of component (b) is contained in a second-part agent (it is to be noted that persulfate which is to be used as a third-part agent is not included in an oxidizing agent as component (b)). As an oxidizing agent, hydrogen peroxide, a generator of a hydrogen peroxide or an oxygen such as urea peroxide, melamine peroxide, sodium perborate, potassium perborate, sodium percarbonate and potassium percarbonate are preferable, and among them, hydrogen peroxide is preferable. The content of an oxidizing agent is preferably 0.1-12 wt. %, more preferably 0.5-9 wt. %, even more preferably 1-6 wt. % in the total composition as converted to the amount of hydrogen peroxide in view of sufficient dying and bleaching effects, reduction in hair damage and scalp irritation.

The composition of the present invention contains (c) ammonia and a salt thereof as an alkaline agent in a first-part agent. As an ammonium salt, ammonium carbonate and ammonium hydrogen carbonate are preferable. Two or more kinds of component (c) can be used in combination, and the content thereof is preferably 0.05-15 wt. %, more preferably 0.1-10 wt. %, even more preferably 0.2-5 wt. % as converted to the amount of ammonia, in view of sufficient dying and bleaching effects and reduction in hair damage and scalp irritation.

As an alkaline agent, alkanolamine and a salt thereof such as monoethanolamine, isopropanolamine, 2-amino-2-methylpropanol and 2-aminobutanol; alkanediamine or a salt thereof such as 1,3-propanediamine; carbonate such as guanidine carbonate, sodium carbonate, potassium carbonate, sodium hydrogen carbonate and potassium hydrogen carbonate can be used in combination in addition to the above-described component (c). Among these alkaline agents except component (c), alkanolamine and a salt thereof are preferable, and monoethanolamine and a salt thereof are more preferable.

In a case when an alkaline agent except component (c) is used in combination, the sum of the content (X), which represents the content of ammonia and a salt thereof as converted to ammonia in the total composition, and the content (Y), which represents the content of monoethanolamine and a salt thereof as converted to monoethanolamine is preferably 0.05-15 wt. %, more preferably 0.1-10 wt. %, even more preferably 0.2-5 wt. % in the total composition in view of sufficient dying and bleaching effects as well as reduction in hair damage, scalp irritation and olfactory stimulation. Further, the weight ratio (i.e., X/Y) is preferably 0.01:1-2:1, more preferably 0.02:1-1:1, even more preferably 0.05:1-0.5:1.

In a case when the composition of the present invention is a bleach composition, it does not contain a dye; and in a case when the composition of the present invention is a dye composition, it contains an oxidation dye intermediate or a direct dye in a first-part agent.

As an oxidation dye intermediate which can be used in the present invention, a known precursor or a coupler which is ordinarily employed in a hair dye is used. A precursor can be, for example, paraphenylenediamine, toluene-2,5-diamine, 2-chloroparaphenylenediamine, N-methoxyethylparaphenylenediamine, N,N-bis(2-hydroxyethyl)paraphenylenediamine, 2-(2-hydroxyethyl)paraphenylenediamine, 2,6-dimethylparaphenylenediamine, 4,4'-diaminodiphenylamine, 1,3-bis(N-(2-hydroxyethyl)-N-(4-aminophenyl)amino)-2-propanol, PEG-3,3,2'-paraphenylenediamine, paraaminophenol, paramethylaminophenol, 3-methyl-4-aminophenol, 2-aminomethyl-4-aminophenol, 2-(2-hydroxyethylaminomethyl)-4-aminophenol, orthoaminophenol, 2-amino-5-methylphenol, 2-amino-6-methylphenol, 2-amino-5-acetamidophenol, 3,4-diaminobenzoic acid, 5-aminosalicylic acid, 2,4,5,6-tetraaminopyrimidine, 2,5,6-triamino-4-hydroxypyrimidine, 4,5-diamino-1-(4'-chlorobenzyl)pyrazole, 4,5-diamino-1-hydroxyethylpyrazole, a salt thereof and the like.

A coupler can be, for example, metaphenylenediamine, 2,4-diaminophenoxyethanol, 2-amino-4-(2-hydroxyethylamino)anisole, 2,4-diamino-5-methylphenetol, 2,4-diamino-5-(2-hydroxyethoxy)toluene, 2,4-dimethoxy-1,3-diaminobenzene, 2,6-bis(2-hydroxyethylamino)toluene, 2,4-diamino-5-fluorotoluene, 1,3-bis(2,4-diaminophenoxy)propane, metaaminophenol, 2-methyl-5-aminophenol, 2-methyl-5-(2-hydroxyethylamino)phenol, 2,4-dichloro-3-aminophenol, 2-chloro-3-amino-6-methylphenol, 2-methyl-4-chloro-5-aminophenol, N-cyclopentyl-metaaminophenol, 2-methyl-4-methoxy-5-(2-hydroxyethylamino)phenol, 2-methyl-4-fluoro-5-aminophenol, resorcin, 2-methylresorcin, 4-chlororesorcin, 1-naphthol, 1,5-dihydroxynaphthalene, 1,7-dihydroxynaphthalene, 2,7-dihydroxynaphthalene, 2-isopropyl-5-methylphenol, 4-hydroxyindole, 5-hydroxyindole, 6-hydroxyindole, 7-hydroxyindole, 6-hydroxybenzomorpholine, 3,4-methylenedioxyphenol, 2-bromo-4,5-methylenedioxyphenol, 3,4-methylenedioxyaniline, 1-(2-hydroxyethyl)amino-3,4-methylenedioxybenzene, 2,6-dihydroxy-3,4-dimethylpyridine, 2,6-dimethoxy-3,5-diaminopyridine, 2,3-diamino-6-methoxypyridine, 2-methylamino-3-amino-6-methoxypyridine, 2-amino-3-hydroxypyridine, 2,6-diaminopyridine, a salt thereof and the like.

For each of the precursor and the coupler, two or more kinds can be used in combination, and the content thereof is each preferably 0.01-5 wt. %, more preferably 0.1-4 wt. % in the total composition.

A direct dye which is used in the present invention can be, for example, an acid dye, a nitro dye, a disperse dye, a basic dye, a direct dye as disclosed in JP-A-2003-342139. An acid dye can be, for example, Blue No. 1, Violet No. 401, Black No. 401, Orange No. 205, Red No. 227, Red No. 106, Yellow No. 203 and Acid Orange No. 3. A nitro dye can be, for example, 2-nitroparaphenylenediamine, 2-amino-6-chloro-4-nitrophenol, 3-nitro-p-hydroxyethylaminophenol, 4-nitro-orthophenylenediamine, 4-amino-3-nitrophenol, 4-hydroxypropylamino-3-nitrophenol, HC Blue No. 2, HC Orange No. 1, HC Red No. 1, HC Yellow No. 2, HC Yellow No. 4, HC Yellow No. 5, HC Red No. 3 and N,N-bis-(2-hydroxyethyl)-2-nitroparaphenylenediamine. A disperse dye can be, for example, Disperse Violet No. 1, Disperse Blue No. 1, Disperse Black No. 9. A basic dye can be, for example, Basic Blue No. 99, Basic Brown No. 16, Basic Brown No. 17, Basic Red No. 51, Basic Yellow No. 57, Basic Yellow No. 87 and Basic Orange No. 31.

Two or more kinds of direct dyes can be used in combination, and further they can be used with an oxidation dye intermediate in combination. The content thereof is preferably 0.001-5 wt. %, more preferably 0.01-3 wt. % in the total composition.

In the hair dye composition of the present composition, it is preferable that a cationic polymer is additionally contained in any one or more of a first-part agent, a second-part agent and a third-part agent for providing an excellent feeling upon application. A cationic polymer refers to a polymer having a cationic group or a group which can be ionized to a cationic group, and it generally includes an amphoteric polymer which can be cationic as a whole. In other words, a cationic polymer can be the one which contains an amino group or an ammonium group in the side chain of a polymer or the one which is a solution containing a diallyl quaternary ammonium salt in its constitutional unit; for example, a cationized cellulose derivative, a cationic starch, a cationized guar gum derivative, a polymer or a copolymer of diallyl quaternary ammonium salt, a quaternarized polyvinylpyrrolidone derivative. Among them, a polymer containing a diallyl quaternary ammonium salt in its constitutional unit, a quaternarized polyvinylpyrrolidone derivative and a cationized cellulose derivative are preferable, and among them, a polymer or a copolymer of diallyl quaternary ammonium salt and a cationized cellulose derivative are more preferable, and of these, a polymer or a copolymer of diallyl quaternary ammonium salt is even more preferable. As a skeletal structure of a copolymer of diallyl quaternary ammonium salt, the one represented by formula (20) or (21) below is preferable.

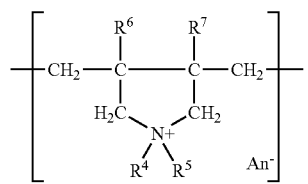

(20)

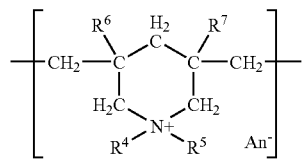

(21)

(Wherein $R^4$ and $R^5$ can be the same or different from one another and each represents a hydrogen atom, a $C_{1-18}$ alkyl group, an aryl (phenyl and the like) group, a hydroxyalkyl group, an amidoalkyl group, a cyanoalkyl group, an alkoxyalkyl group or a carboalkoxyalkyl group; $R^6$ and $R^7$ can be the same or different from one another and each represents a hydrogen atom, a $C_{1-3}$ alkyl group or phenyl group; and An⁻ represents an anion (chloride ion, bromide ion, iodide ion, sulfate anion, sulfonate anion, methyl sulfate anion, phosphate anion, nitrate anion, and the like).

A monomer which constitutes a copolymer with a diallyl quaternary ammonium salt can be acrylic acid, methacrylic acid or a salt of these acids, or acrylamide. Among these, acrylic acid, methacrylic acid and a salt of these acids are preferable. A copolymer of diallyl quaternary ammonium salt and acrylic acid, methacrylic acid or a salt of these acids becomes a cationic polymer as a whole due to a high structural ratio of diallyl quaternary ammonium salt.

Examples of a polymer or a copolymer of diallyl quaternary ammonium salt include a polymer of dimethyl diallylammoniumchloride polymer (polyquaternium-6, e.g., Merquat 100; ONDEO Nalco), a copolymer of dimethyl diallylammonium chloride and acrylic acid (polyquaternium-22, e.g., Merquat 280 and 295; ONDEO Nalco) and a copolymer of dimethyl diallylammoniumchloride and acrylamid (polyquaternium-7, e.g., Merquat 550; ONDEO Nalco) and the like, and among them, Merquat 280 and 295 are preferable.

As a quaternarized polyvinyl pyrrolidone, the one represented by formula (22) is preferable.

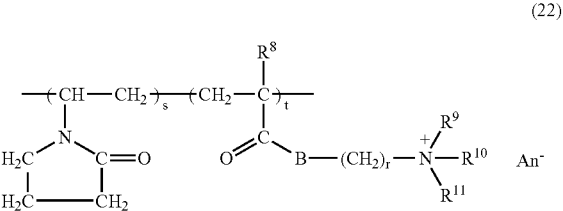

(22)

(Wherein $R^8$ represents a hydrogen or a $C_{1-3}$ alkyl group; $R^9$, $R^{10}$ and $R^{11}$ are the same or different from one another and each represents a hydrogen atom, a $C_{1-4}$ alkyl group, a $C_{1-4}$ hydroxyalkyl group, a $C_{1-4}$ amidoalkyl group, a $C_{1-4}$ cyanoalkyl group, a $C_{1-4}$ alkoxyalkyl group or a $C_{1-4}$ carboalkoxyalkyl group; B represents an oxygen atom or an imino group; r represents an integer of 1-10; s and t represent a number such that the sum of them is 20-8000; An⁻ is as defined above.)

The molecular weight of the quaternarized polyvinyl pyrrolidone derivative used in the present invention is preferably 10,000-2,000,000, more preferably 50,000-1,500,000, and commercial products thereof include Gafquat 734, 755, 755N (all are the products of ISP Japan Ltd.) and the like.

As a cationized cellulose derivative, the one represented by formula (23) below is preferable, for example.

(23)

(wherein G represents a residue as an anhydroglucose unit; f represents an integer of 50-20,000; each of $R_{12}$ represents a substituent represented by formula (24) below.)

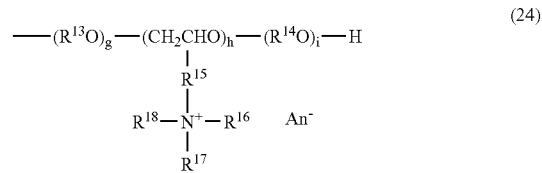

(24)

(wherein $R^{13}$ and $R^{14}$ represents an alkylene group having 2 or 3 carbons; g represents an integer of 0-10; h represents an integer of 0-3; i represents an integer of 0-10; $R^{15}$ represents a $C_{1-3}$ alkylene group or a hydroxyalkylene group; $R^{16}$, $R^{17}$ and $R^{18}$ are the same or different from one another and each represents an alkyl group, an aryl group or an aralkyl group having up to 10 carbons, or they can form a heterocyclic ring containing nitrogen atoms in the formula; An⁻ is defined as above.)

A degree of cation substitution in a cationic cellulose derivative, i.e., an average value of h per anhydroglucose unit, is preferably 0.01-1, more preferably 0.02-0.5. The total of g+i is 1-3 on average. It is insufficient when the degree of cation substitution is below 0.01. The degree of cation substitution can exceed 1; however, it is preferably 1 or less in view of reaction yield. The molecular weight of the cationized cellulose derivative used is preferably 100,000-3,000,000, and commercial products thereof include Leoguard G and GP (products of Lion Corporation), Polymer-JR-125, JR-400, JR-30M, LR-400, LR-30M (all are the products of Union Carbide Corporation) and the like. Other cationized cellulose derivatives include hydroxyethylcellulose dimethyldiallylammoniumchloride, and commercial products thereof include Cellquat H-100 and L-200 (products of National Starch & Chemical).

Two or more kinds of the above-described cationized polymers can be used in combination, and the higher the content thereof, the better the effect is; however, if the content is too high, it causes instability and reduction in viscosity in single use thereof or in mixing. In view of the above, the content thereof is preferably 0.001-20 wt. %, more preferably 0.01-10 wt. %, even more preferably 0.05-5 wt. % in the total composition.

The hair dye composition of the present invention preferably contains additional silicones for providing excellent feeling upon application. Silicones can be polysiloxanes, modified silicones (such as amino-modified silicones, fluorine-modified silicones, alcohol-modified silicones, polyether-modified silicones, epoxy-modified silicones, alkyl-modified silicones and the like) and cyclic polysiloxanes, and among them, polysiloxanes and amino-modified silicones are preferable, and combinational use of dimethylpolysiloxanes and amino-modified silicones is more preferable.

As polysiloxanes, a highly-polymerized silicone having a number-average polymerization degree of 1000 or above is preferable, and the one having a number-average polymerization degree of 1500 or above is more preferable, and the one having a number-average polymerization degree of 2000 or above but less than 20,000 is even more preferable. Examples of a commercial product of a highly-polymerized silicone having a number-average polymeration degree of 1000 or above include SH200-1,000,000cs (Dow Corning Toray Co., Ltd), TSF451-100MA (GE Toshiba Silicones Co., Ltd.), BY11-026 (Dow Corning Toray Co., Ltd; a solution of a highly-polymerized silicone diluted with a low-viscosity silicone), KF9008 (Shin-Etsu Chemical Co., Ltd.; a solution of a highly-polymerized silicone diluted with a cyclic silicone), BY22-050A (Dow Corning Toray Co., Ltd; a cationic emulsion of a highly-polymerized silicone), BY22-060 (Dow Corning Toray Co., Ltd; a cationic emulsion of a solution in which a highly-polymerized silicone is diluted with a low-viscosity silicone), BY22-020 (Dow Corning Toray Co., Ltd; a cationic emulsion of a solution in which a highly-polymerized silicone is diluted with liquid paraffin), KM904 (Shin-Etsu Chemical Co., Ltd.; a cationic emulsion of a solution in which a highly-polymerized silicone is diluted with a low-viscosity silicone) and the like.

An amino-modified silicone can be a silicone having an amino group or an ammonium group, and examples thereof are amino-modified silicone oil in which all or a part of the terminal hydroxy groups are blocked with a methyl group or the like, amodimethicone in which the termini are not blocked, and the like. A preferable amino-modified silicone is the one represented by formula (25) below.

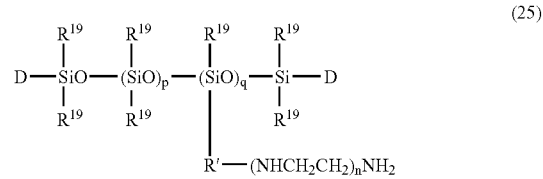

(wherein $R^{19}$ represents a hydroxy group, a hydrogen atom or R; R represents a substituted or unsubstituted monovalent $C_{1-20}$ hydrocarbon group; D represents an R, —R'—(NHCH$_2$CH$_2$)$_n$NH$_2$, an OR group or a hydroxy group; R' represents a divalent $C_{1-8}$ hydrocarbon group; n represents a number of 0-3; p and q represents a number such that the sum of them is 10 or more but less than 20,000, preferably 10 or more but less than 3000, more preferably 30 or more but less than 1000, even more preferably 40 or more but less than 800 on number average. An amino equivalent weight is 200 g/mol-100,000 g/mol, preferably 200 g/mol-30,000 g/mol, more preferably 400 g/mol-10,000 g/mol, even more preferably 600 g/mol-5000 g/mol.)

Preferable commercial products of an amino-modified silicone include amino-modified silicone oil such as SF8451C (Dow Corning Toray Co., Ltd.; viscosity 600 mm²/s, amino equivalent weight 1700 g/mol), SF8452C (Dow Corning Toray Co., Ltd.; viscosity 700 mm²/s, amino equivalent weight 6400 g/mol), SF8457C (Dow Corning Toray Co., Ltd.; viscosity 1200 mm²/s, amino equivalent weight 1800 g/mol), KF8003 (GE Toshiba Silicones Co., Ltd., viscosity 1850 mm²/s, amino equivalent weight 2000 g/mol), KF867 (GE Toshiba Silicones Co., Ltd., viscosity 1300 mm2/s, amino equivalent weight 1700 g/mol) and the like, or amodimethicone emulsion such as SM8704C (Dow Corning Toray Co., Ltd., amino equivalent weight 1800 g/mol) and the like.

Further, a copolymer containing a block chain of an amino-modified organopolysiloxane chain and a polyoxyalkylene chain can be used. For example, the one represented by formula (26) below can be used, and examples of commercial products include FZ-3789, silicone SS-3588 (both are products of Dow Corning Toray Co., Ltd.) and the like.

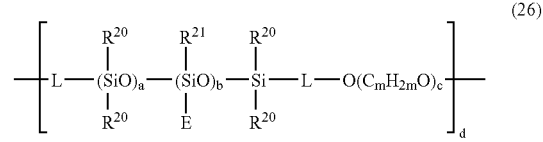

(wherein $R^{20}$ represents a hydrogen atom or a monovalent $C_{1-6}$ hydrocarbon group; $R^{21}$ represents $R^{20}$ or E; E represents a group represented by —$R^{22}$-J (wherein $R^{22}$ represents a bond or a divalent $C_{1-20}$ hydrocarbon group; J represents a group containing a primary to tertiary amino group or a group containing an ammonium group); L represents a divalent group; a represents a number of 2 or more; b represents a number of 1 or more; m represents a number of 2-10; c represents a number of 4 or more; d represents a number of 2 or more. Plural numbers of $R^{20}$, $R^{21}$ and E can be the same or different from one another.)

Further, amino-modified silicone oil can be mixed in as an emulsion. An emulsion of amino-modified silicone can be prepared by mechanical emulsion (high-shear mechanical mixing of an amino-modified silicone and water), chemical emulsion (emulsifying an amino-modified silicone with water or an emulsifying agent), or a combination of these methods, or by emulsion polymerization.

The total content of silicones is preferably 0.02-40 wt. %, more preferably 0.1-20 wt. %, even more preferably 0.2-15 wt. % in the total composition in view of providing a sufficient effect and suppression of stickiness. Further, the content ratio of each silicone is preferably in such a range that the converted amino equivalent weight denoted by the following formula is 500-100,000 g/mol, more preferably 1000-80,000 g/mol, even more preferably 2000-50,000 g/mol.

Converted amino equivalent weight (g/mol)=(total weight of all the silicones per gram of the total composition (g/g))/ (total number of moles of an amino group, an imino group and an ammonium group in an amino-modified silicone per gram of the total composition (mol/g))

"Total weight of all the silicones per gram of the total composition (g/g)" and "total number of moles of an amino group, an imino group and an ammonium group in amino-modified silicone per gram of the total composition (mol/g)" are obtained as follows.

Silicones are fractionated from each of a first-part agent and a second-part agent (in a case of a three-part agent, furthermore from a third-part agent), and then the total weight (g) of all the silicones and the total number of moles (mol) of an amino group, an imino group and an ammonium group in an amino-modified silicone in each agent is quantified. Then by counting the mixing ratio of each agent in the total composition, the total weight of all the silicones per gram of the total composition (g/g) and the total number of moles of an amino group, an imino group and an ammonium group in an amino-modified silicone per gram of the total composition (mol/g) are calculated. Then a converted amino equivalent weight (g/mol) is calculated using the formula for amino equivalent weight conversion described above.

A weight ratio of a cationic polymer (active amount):silicones is preferably 50:1-1:50, and more preferably 50:1-1:10 in a case when the composition contains silicones.

The composition of the present invention preferably contains a higher alcohol in any one or more of a first-part agent, a second-part agent and a third-part agent in view of improvement in a feeling and stability. Higher alcohols have an effect of improving the feeling upon rinsing, while they prevent separation by forming a structural body with a surfactant. A higher alcohol is preferably the one having a carbon number of 8-22, more preferably the one having a carbon number of 16-22, and examples thereof include cetylalcohol, stearyl alcohol, behenyl alcohol and the like, and a mixture of these alcohols.

Two or more kinds of higher alcohols can be used in combination, and the content thereof is preferably 0.01-20 wt. %, more preferably 0.1-10 wt. % in the total composition.

The hair dye composition of the present invention can contain a surfactant in either or both of a first-part agent and a second-part agent. As a surfactant, any one of a cationic surfactant, a non-ionic surfactant, an amphoteric surfactant and an anionic surfactant can be used.

A cationic surfactant includes a primary to tertiary amine-type compound and a quaternary ammonium salt-type compound. Among them, a quaternary ammonium salt-type compound represented by formula (27) below and a tertiary amine-type compound represented by formula (28) below are preferable.

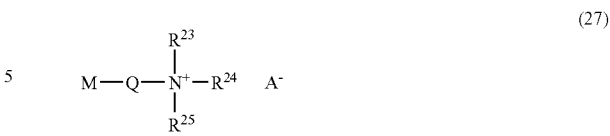

(wherein M represents a hydrogen atom or linear or branched, saturated or unsaturated amido group, N-hydrocarbon carbamoyl group, an acyloxy group or a hydrocarbonoxy group having a total carbon number of 12-24; Q represents linear or branched, saturated or unsaturated divalent $C_{1-25}$ hydrocarbon group which may contain a hydroxy group; at least one of $R^{23}$, $R^{24}$ and $R^{25}$ represents linear or branched $C_{1-25}$ alkyl group or alkenyl group, while the rest is $C_{1-3}$ alkyl group; $A^-$ represents a halogenated ion or an organic anion.

(wherein M and Q are as defined above; each of $R^{26}$ and $R^{27}$ independently represents $C_{1-4}$ alkyl group.)

A quaternary ammonium salt represented by formula (27) can be a mono-long chain alkyl quaternary ammonium salt ($C_{12-25}$), a di-long chain alkyl or alkenyl quaternary ammonium salt ($C_{12-25}$), a branched alkyl quaternary ammonium salt ($C_{12-25}$), an alkylamido ($C_{12-24}$) alkyl ($C_{1-5}$) quaternary ammonium salt, a N-hydrocarbon carbamoyl ($C_{12-24}$) alkyl ($C_{1-5}$) quaternary ammonium salt, an acyl ($C_{12-24}$) oxyalkyl ($C_{1-5}$) quaternary ammonium salt, an alkyl or alkenyl ($C_{12-24}$) oxyalkyl ($C_{1-5}$) quaternary ammonium salt.

A mono-long chain alkyl quaternary ammonium salt ($C_{12-25}$) can be stearyltrimethylammonium chloride, myristyltrimethylammonium chloride, cetyltrimethylammonium chloride, arachyltrimethylammonium chloride, behenyltrimethylammonium chloride, lauryltrimethylammonium chloride and the like.

A di-long chain alkyl or alkenyl quaternary ammonium salt ($C_{12-25}$) can be distearyldimethylammonium chloride, dioleyldimethylammonium chloride, diisostearyldimethylammonium methosulfate, di((2-dodecanoylamino)ethyl)dimethylammonium chloride, di((2-stearoylamino)propyl) dimethylammonium ethsulfate and the like.

A branched alkyl quaternary ammonium salt ($C_{12-25}$) can be 2-decyltetradecyltrimethylammonium chloride, 2-dodecylhexadecyltrimethylammonium chloride, di-2-hexyldecyldimethylammonium chloride, di-2-octyldodecyldimethylammonium chloride and the like.

An alkylamido ($C_{12-24}$) alkyl ($C_{1-5}$) quaternary ammonium salt can be a stearamidopropyl quaternary ammonium salt. A N-hydrocarbon carbamoyl ($C_{12-24}$) alkyl ($C_{1-5}$) quaternary ammonium salt can be a N-stearylcarbamoylpropyl quaternary ammonium salt. An acyl ($C_{12-24}$) oxyalkyl ($C_{1-5}$) quaternary ammonium salt can be a stearoyloxypropyl quaternary ammonium salt. A hydrocarbon ($C_{12-24}$) oxyalkyl ($C_{1-5}$) quaternary ammonium salt can be an octadecyloxypropyltrimethylammonium chloride.

Among the quaternary ammonium salts represented by formula (27), the one in which M is a hydrogen atom; Q is a divalent $C_{8-25}$ saturated hydrocarbon group; $R^{23}$ is a methyl group or a $C_{8-25}$ alkyl group; $R^{24}$ and $R^{25}$ are a methyl group is preferable.

In the tertiary amine-type compound represented by formula (28), M is preferably an amido group or a hydrocarbon oxy group having a total carbon number of 14-22, more preferably having a total carbon number of 18-22, when M is other than a hydrogen atom. Further, the hydrocarbon part thereof is preferably saturated, and more preferably it is linear. Q in this case is preferably a trimethylene group or a 2-hydroxytrimethylene group. When M is a hydrogen atom, Q is preferably a group having a carbon number of 18-25, more preferably it is saturated, and even more preferably it is linear, and further preferably it contains a hydroxy group. $R^{26}$ and $R^{27}$ can be a methyl group, an ethyl group, a propyl group, an isopropyl group, a butyl group, a t-butyl group, and among them, a methyl group and an ethyl group are preferable, and a methyl group is more preferable.

Preferable forms of the tertiary amine-type compound represented by formula (28) are an etheramine compound represented by formula (28a) and an amido amine compound represented by formula (28b).

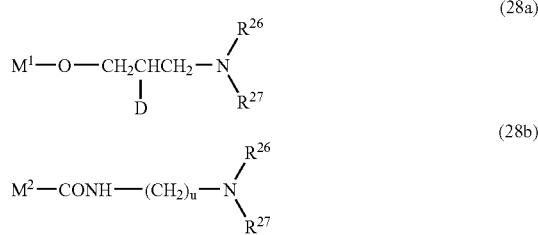

(wherein $R^{26}$ and $R^{27}$ are defined as above; $M^1$ represents linear or branched, saturated or unsaturated $C_{12-24}$ hydrocarbon group; D represents a hydrogen atom or a hydroxy group; $M^2$ represents linear or branched, saturated or unsaturated $C_{11-23}$ hydrocarbon group; u represents a number of 2-4.)

Examples of an etheramine compound represented by formula (28a) include N,N-dimethyl-3-hexadecyloxypropylamine (hexadecyloxypropyldimethylamine), N,N-dimethyl-3-octadecyloxypropylamine (octadecyloxypropyldimethylamine), N,N-dimethyl-3-hexadecyloxy-2-hydroxypropylamine (hexadecyloxy(2-hydroxypropyl)dimethylamine), N,N-dimethyl-3-octadecyloxy-2-hydroxypropylamine (octadecyloxy(2-hydroxypropyl) dimethylamine), N,N-dimethyl-3-behenyloxy-2-hydroxypropylamine (behenyloxy(2-hydroxypropyl) dimethylamine) and the like. Examples of the commercial products thereof include Catinal SHPA (TOHO Chemical Industry Co., LTD.; N,N-dimethyl-3-octadecyloxy-2-hydroxypropylamine, INCI name: stearyl PG-dimethylamine).

An amido amine compound represented by formula (28b) is highly adhesive to the hair, and thus impart the hair a silky feeling in rinsing and drying, and it further contributes to the dispersive stability of other components. Examples of an amido amine compound include isostearamidoethyl diethylamine, oleamidoethyl diethylamine, stearamidoethyl diethylamine, stearamidopropyl diethylamine, stearamidoethyl dibutylamine, stearamidopropyl dibutylamine, stearamidopropyl dipropylamine, stearamidoethyl dipropylamine, stearamidoethyl dimethylamine, stearamidopropyl dimethylamine, palmitamidoethyl diethylamine, palmitamidopropyl diethylamine, palmitamidoethyl dimethylamine, palmitamidopropyl dimethylamine, myristamidoethyl dimethylamine, myristamidopropyl dimethylamine, behenamidoethyl diethylamine, behenamidopropyl diethylamine, behenamidoethyl dimethylamine, behenamidopropyl dimethylamine, arachylamidoethyl dimethylamine, arachylamidopropyl dimethylamine and the like. Among them, stearamidoethyl diethylamine, stearamidopropyl dimethylamine, behenamidopropyl dimethylamine and the like are preferable in view of quality, stability and availability (i.e., easily obtainable).

It is preferable that an amine in a primary to tertiary amine-type compound is in a separated state when the compound is used, which state is prepared by making it acidic by letting it form an acid addition salt by addition of equivalent mole or more of an acid. At this point at least one kind of water soluble organic acid is preferably used as an acid for formation of an acid addition salt. A water soluble organic acid can be alkyl sulfuric acid, alkyl phosphoric acid, monocarboxylic acid, dicarboxylic acid, hydroxycarboxylic acid, polycarboxylic acid, acidic amino acid and the like. Among them, carboxylic acid and acidic amino acid are preferable, and as a carboxylic acid, dicarboxylic acid and hydroxycarboxylic acid are preferable. Dicarboxylic acid can be malonic acid, succinic acid, glutalic acid, adipic acid, maleic acid, fumaric acid and phthalic acid, and among them, malonic acid, succinic acid and maleic acid are preferable. Hydroxycarboxylic acid can be glycolic acid, lactic acid, hydroxyacrylic acid, oxybutyric acid (preferably α-oxybutyric acid), glyceric acid, malic acid, tartaric acid and citric acid, and among them, α-hydroxycarboxylic acid is preferable, and glycolic acid, lactic acid and malic acid are more preferable. Acidic amino acid can be L-glutamic acid and L-aspartic acid, and among them, L-aspartic acid is preferable. The mixing amount of the above-described organic acid is preferably 0.8-10 times, more preferably 1.5-10 times in terms of moles to the primary to tertiary amine compound in view of reduction in amine-derived odor, softness and heightening of conditioning effects such as smoothness.

A non-ionic surfactant can be polyoxyalkylene alkyl ether, polyoxyalkylene alkenyl ether, higher fatty acid sucrose ester, polyglycerine fatty acid ester, higher fatty acid mono or diethanolamide, polyoxyethylene hydrogenated castor oil, polyoxyethylenesorbitan fatty acid ester, polyoxyethylenesorbit fatty acid ester, alkylsaccharide surfactant, alkylaminoxide, alkylamido amineoxide and the like. Among them, polyoxyalkylene alkyl ether and polyoxyethylene hydrogenated castor oil are preferable, and among them polyoxyalkylene alkyl ether is more preferable.

An amphoteric surfactant can be imidazoline type, carbobetaine type, amidobetaine type, sulfobetaine type, hydroxysulfobetaine type and amidosulfobetaine type and the like.

An anionic surfactant can be alkylbenzensulfonate, alkyl or alkenylether sulfate, alkyl or alkenyl sulfate, olefinsulfonate, alkanesulfonate, saturated or unsaturated fatty acid salt, alkyl or alkenylether carboxyate, α-sulfo fatty acid salt, N-acylamino acid-type surfactant, phosphoric acid mono or diester-type surfactant, sulfosuccinic ester and the like. A counter ion to the anionic residue of the above-described surfactants can be an alkali metal ion such as a sodium ion and a potassium ion; an alkaline earth metal ion such as a calcium ion and a magnesium ion; an ammonium ion; an alkanolamine containing 1-3 alkanol group having a carbon number of 2 or 3 (e.g.,monoethanolamine, diethanolamine, triethanolamine, triisopropanolamine and the like).

Among the above surfactants, a cationic surfactant is preferable since it is capable of further enhancing the effect of the present invention. A surfactant can be used singly or in combination of two or more kinds, and the content thereof is preferably 0.01-20 wt. %, more preferably 0.05-5 wt. % in the total composition in view of the stability of the composition and the feeling. The content is an amount converted to the primary to tertiary amine-type compound, in a case when the surfactant is a salt of a primary to tertiary amine-type compound.

In the composition of the present invention, water and, if necessary, an organic solvent are used as a solvent. An organic solvent can be lower alkanols such as ethanol and 2-propanol; aromatic alcohols such as benzyl alcohol and benzyloxyethanol; polyols such as propylene glycol, 1,3-butanediol, diethylene glycol and glycerin; cellosolves such as ethyl cellosolve and butyl cellosolve; carbitols such as ethyl carbitol and butyl carbitol.

The composition of the present invention can contain additional components which are ordinarily employed as a cosmetic material other than the ones described above, and such components can be hydrocarbons, animal/plant oil and fat, higher fatty acids, natural or synthetic polymers, ether, protein derivatives, protein hydrolysis, amino acids, antiseptic, chelating agents, stabilizers, antioxidants, plant extracts, crude drug extracts, vitamins, perfumes and ultraviolet absorbers.

In the hair dye agent of the present invention, a first-part agent and a second-part agent can be prepared into, for example, liquid, emulsion, cream, gel, paste, mousse and the like, or they can be prepared into aerosol. A first-part agent and a second-type agent (and further, a third-part agent in a case of a three-part type composition) preferably has such a viscosity that they do not easily drip when applied to the hair, and the viscosity is preferably 2000-100,000 mm$^2$/s at 25° C. as measured by a B-type rotating viscometer equipped with a helical stand (B8R-type viscometer, TOKIMEC Inc.). At this point the viscosity refers to a value measured after spinning the agent for one minute at 10 rpm using a rotor T-C.

<Method for Dying the Hair>

For carrying out a hair dying treatment using the composition of the present invention, for example, mix a first-part agent and a second-part agent (and further, a third-part agent in a case of a three-part type composition) of the composition of the present invention right before use; and apply to the hair; and wash it off and dry the hair after letting it stand for a predetermined time. Temperature upon application to the hair is preferably 15-45° C. Time during which the hair is left to stand is preferably within 1 hour, more preferably 3-45 minutes, even more preferably 5-30 minutes, even more preferably 10-30 minutes. In this case a good conditioning effect is obtained when the hair dye is lightly washed off with water and subsequently washed with a shampoo containing an anionic surfactant and followed by a washing with water, since a certain amount of cationic polymer is eluted off, while a certain amount of silicones remains on the hair. As a shampoo, a conventional aqueous shampoo containing an anionic surfactant such as laules-1 sodium sulfate, laules-2 sodium sulfate and laules-3 sodium sulfate and the like at 5-20 wt. % is preferable.

The following examples further describe and demonstrate embodiments of the present invention. The examples are given solely for the purpose of illustration and are not to be construed as limitations of the present invention.

EXAMPLE

Examples 1-12 and Comparative Example 1-3

A first-part agent shown in Tables 1-4, a second-part agent shown in Table 5 and a third-part agent shown in Table 6 are prepared. Agents of Examples 1, 2, 4-12 and Comparative Examples 1-3 contain a dye, and thus they are used as a hair dye. Agent of Example 3 does not contain a dye, and thus it is used as a bleaching agent.

TABLE 1

A first-part agent

| | Wt. % | | | |
|---|---|---|---|---|
| | Example 1 | Example 2 | Example 3 | Comparative Example 1 |
| Glycine betaine (formula (2)) | 6.00 | 6.00 | 6.00 | — |
| p-Aminophenol | 0.25 | 0.15 | — | 0.25 |
| m-Aminophenol | — | 0.32 | — | — |
| Toluene-2,5-diamine | 0.09 | 0.21 | — | 0.09 |
| 5-Amino-o-cresol | 0.37 | — | — | 0.37 |
| Propylene glycol | 4.00 | 4.00 | 4.00 | 4.00 |
| Ascorbic acid | 0.40 | 0.40 | 0.40 | 0.40 |
| Anhydrous sodium sulfite | 0.40 | 0.40 | 0.40 | 0.40 |
| EDTA-4Na dihydrate | 0.10 | 0.10 | 0.10 | 0.10 |
| Stearyl trimoniumchloride | 5.00 | 5.00 | 5.00 | 5.00 |
| Ceteth-40 | 2.50 | 2.50 | 2.50 | 2.50 |
| Cetearyl alcohol | 8.00 | 8.00 | 8.00 | 8.00 |
| Amino-modified silicone*[1] | 3.00 | 3.00 | 3.00 | 3.00 |
| Ethanolamine | 1.50 | 1.50 | 1.50 | 1.50 |
| Ammonia (28 wt. %) | 6.50 | 6.50 | 6.50 | 6.50 |
| Perfume | 0.50 | 0.50 | 0.50 | 0.50 |
| Ammonium hydrogen carbonate*[2] | q.s | q.s | q.s | q.s |
| Purified water | Balance | Balance | Balance | Balance |
| Total | 100.0 | 100.0 | 100.0 | 100.0 |

*[1]SM8704C, Dow Corning Toray Co., Ltd.
*[2]Amount necessary to adjust pH to 10

TABLE 2

A first-part agent

| | Wt. % | | | |
|---|---|---|---|---|
| | Example 4 | Example 5 | Example 6 | Comparative Example 2 |
| Hydrochloride of betaine compound (8) | 6.0 | 6.0 | 6.0 | — |
| p-Aminophenol | 0.3 | 0.1 | — | 0.3 |
| Toluene-2,5-diamine sulfate | 0.2 | — | 0.2 | 0.2 |
| 5-Amino-o-cresol | — | — | 0.2 | — |
| m-Aminophenol | 0.2 | 0.1 | — | 0.2 |
| Basic blue 99 | — | — | 0.2 | — |
| Basic brown 16 | — | 0.1 | — | — |
| HC Yellow 4 | 0.05 | — | — | 0.05 |
| HC Yellow 2 | — | 0.05 | — | — |
| Direct dye (P) | — | 0.05 | — | — |
| Direct dye (Q) | 0.05 | — | — | 0.05 |
| Direct dye (R) | — | — | 0.05 | — |
| Behentrimonium chloride | 2.1 | 2.1 | 2.1 | 2.1 |
| Liquid paraffin | 0.5 | 0.5 | 0.5 | 0.5 |
| Propylene glycol | 7.0 | 7.0 | 7.0 | 7.0 |
| Cetostearyl alcohol | 7.0 | 7.0 | 7.0 | 7.0 |
| Polyquaternium-10*[3] | 1.0 | 1.0 | 1.0 | 1.0 |
| Amino-modified silicone*[4] | 1.5 | 1.5 | 1.5 | 1.5 |
| Ammonia (28 wt. %) | 6.5 | 6.5 | 6.5 | 6.5 |
| Ammonium chloride*[5] | q.s | q.s | q.s | q.s |
| Purified water | Balance | Balance | Balance | Balance |
| Total | 100.0 | 100.0 | 100.0 | 100.0 |

*[3]Ucare Polymer JR-400, Amerchol Corporation
*[4]SM8704C, Dow Corning Toray Co., Ltd.
*[5]Amount necessary to adjust pH to 10

TABLE 3

A first-part agent

| | Wt. % | | | |
|---|---|---|---|---|
| | Example 7 | Example 8 | Example 9 | Comparative Example 3 |
| Glycine betaine (formula (2)) | 6.00 | 6.00 | 6.00 | — |
| p-Aminophenol | 0.25 | 0.15 | 0.20 | 0.25 |
| m-Aminophenol | — | 0.32 | — | — |
| Toluene-2,5-diamine | 0.09 | 0.21 | 0.20 | 0.09 |
| 5-Amino-o-cresol | 0.37 | — | 0.20 | 0.37 |
| Propylene glycol | 4.00 | 4.00 | 4.00 | 4.00 |
| Ascorbic acid | 0.40 | 0.40 | 0.40 | 0.40 |
| Anhydrous sodium sulfite | 0.40 | 0.40 | 0.40 | 0.40 |
| EDTA-4Na | 0.10 | 0.10 | 0.10 | 0.10 |
| Sodium lauryl sulfate | 1.00 | 1.00 | 1.00 | 1.00 |
| Ceteth-40 | 2.50 | 2.50 | 2.50 | 2.50 |
| Cetearyl alcohol | 8.00 | 8.00 | 8.00 | 8.00 |
| Amino-modified silicone[*6] | 3.00 | 3.00 | 3.00 | 3.00 |
| Ethanolamine | 1.50 | 1.50 | 1.50 | 1.50 |
| Ammonia (28 wt. %) | 6.50 | 6.50 | 6.50 | 6.50 |
| Perfume | 0.50 | 0.50 | 0.50 | 0.50 |
| Ammonium hydrogen carbonate[*7] | q.s | q.s | q.s | q.s |
| Purified water | Balance | Balance | Balance | Balance |
| Total | 100.0 | 100.0 | 100.0 | 100.0 |

[*6]SM8704C, Dow Corning Toray Co., Ltd.
[*7]Amount necessary to adjust pH to 10

TABLE 4

A first-part agent

| | Wt. % | | |
|---|---|---|---|
| | Example 10 | Example 11 | Example 12 |
| Hydrochloride of betaine compound (8) | 6.0 | 6.0 | 6.0 |
| p-Aminophenol | 0.3 | 0.1 | — |
| Toluene-2,5-diamine sulfate | 0.2 | — | 0.2 |
| 5-Amino-o-cresol | — | — | 0.2 |
| m-Aminophenol | 0.2 | 0.1 | — |
| Basic blue 99 | — | — | 0.2 |
| Basic brown 16 | — | 0.1 | — |
| HC Yellow 4 | 0.05 | — | — |
| HC Yellow 2 | — | 0.05 | — |
| Direct dye (P) | — | 0.05 | — |
| Direct dye (Q) | 0.05 | — | — |
| Direct dye (R) | — | — | 0.05 |
| Sodium polyoxyethylene (2) lauryl ether sulfate | 3.0 | 3.0 | 3.0 |
| Liquid paraffin | 0.5 | 0.5 | 0.5 |
| Propylene glycol | 7.0 | 7.0 | 7.0 |
| Cetostearyl alcohol | 7.0 | 7.0 | 7.0 |
| Ammonia (28 wt. %) | 6.5 | 6.5 | 6.5 |
| Ammonium chloride[*8] | q.s | q.s | q.s |
| Purified water | Balance | Balance | Balance |
| Total | 100.0 | 100.0 | 100.0 |

[*8]Amount necessary to adjust pH to 10

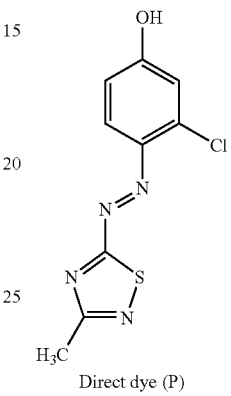

Direct dye (P)

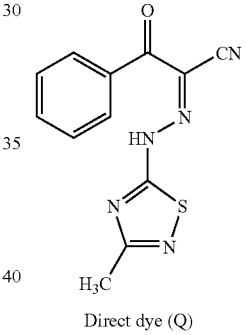

Direct dye (Q)

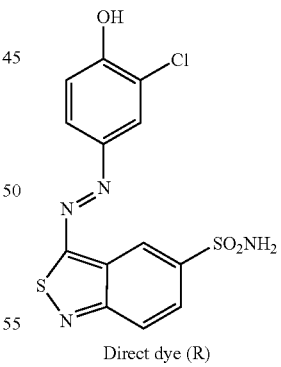

Direct dye (R)

TABLE 5

A second-part agent

| | Wt. % Second-part agent |
|---|---|
| Cetanol | 2.0 |
| Sodium lauryl sulfate | 1.0 |

TABLE 5-continued

A second-part agent

| | Wt. %<br>Second-part agent |
|---|---|
| Hydrogen peroxide (35 wt. %) | 17.0 |
| Methyl paraben | 0.1 |
| Phosphoric acid*[9] | q.s |
| Purified water | Balance |
| Total | 100.0 |

*[9] Amount necessary to adjust pH to 3.5

TABLE 6

A third-part agent (granulated substance)

| | Wt. %<br>Third-part agent |
|---|---|
| Sodium persulfate | 10.0 |
| Potassium persulfate | 16.0 |
| Ammonium persulfate | 26.0 |
| Anhydrous sodium metasilicate | 20.0 |
| Sodium silicate | 17.8 |
| Anhydrous silicic acid | 1.0 |
| Sodium stearate | 5.0 |
| Sodium lauryl sulfate | 1.0 |
| Anhydrous EDTA-4Na | 1.0 |
| β-cyclodextrin | 0.2 |
| Xanthan gum | 1.2 |
| Carboxymethylcellulose sodium | 1.0 |
| Total | 100.0 |

<Dying Procedure>

Each of first-part agents shown in Tables 1-4 was mixed with a second-part agent shown in Table 5 at a weight ratio of 1:2, and the mixture was applied to a hair tress at a bath ratio (agent:hair) of 1:1. The hair tress was left to stand for 30 minutes at 25° C., and subsequently rinsed with water (temperature: approximately 40° C.). The tress was then washed with a commercial shampoo and washed with water, and then a commercial hair rinse was applied. The tress was then rinsed with water and wiped with a towel, and then dried.

<Organoleptic Evaluation>

A hair tress made of hair which had never received a chemical treatment and a hair tress made of heavily deteriorated hair due to repetitive chemical treatments such as dying (i.e., damaged hair) were dyed in accordance with the above-described dying procedure. An organoleptic evaluation was conducted by running a finger through the hair tress, and scores were recorded with respect to a feeling that fingers do not run through smoothly, a feeling of friction and a rough feeling based on the below-described standard.

A: It was felt that fingers almost perfectly ran through the hair, and neither a feeling of friction nor a rough feeling was felt.
B: It was felt that fingers got caught in a tangle a little; however, neither a feeling of friction nor a rough feeling was felt.
C: It was felt that fingers got caught in a tangle a little, and a feeling of friction and a rough feeling were also felt.
D: It was strongly felt that fingers got caught in a tangle, and the hair was frictional and rough.
E: Fingers did not run through, and the hair was greatly frictional and rough.

<Evaluation on Dying Effect>

The hue of the hair tress dyed in accordance with the above-described dying procedure was measured by CIE color system (L*, a* and b*) using a calorimeter (calorimeter CR-400, Konica Minolta Holdings, Inc.), and ΔE* was calculated by the following formula. The bigger the ΔE* is, the better the dying effect is. The result is shown in Table 7.

$$\Delta E^* = \sqrt{(L^*_2 - L^*_1)^2 + (a^*_2 - a^*_1)^2 + (b^*_2 - b^*_1)^2}$$

(wherein $L^*_1$, $a^*_1$ and $b^*_1$ were the value before dying, and $L^*_2$, $a^*_2$ and $b^*_2$ were the value after dying.)

TABLE 7

(Results obtained by use of a first-part agent shown in Table 1 or 3 and a second-part agent shown in Table 5)

| | Score of organoleptic evaluation | | Dying effect ΔE* | |
|---|---|---|---|---|
| First-part agent | Untreated hair | Damaged hair | Untreated hair | Damaged hair |
| Example 1 | A | C | 7.7 | 7.2 |
| Comparative Example 1 | B | D | 7.3 | 6.2 |
| Example 7 | B | D | 7.8 | 7.4 |
| Comparative Example 3 | C | E | 7.5 | 6.5 |

In both cases of the untreated hair and the damaged hair, in dying with a dye containing glycine betaine, the score obtained by an organoleptic evaluation was more than equivalent to the score obtained in a case in which dying was performed with a dye which does not contain glycine betaine. Regarding the dying effect, it appeared to be slightly better in Examples than in Comparative Examples with respect to the untreated hair; however, the dying effect was far better in Examples than in Comparative Examples with respect to the damaged hair. This suggested that the hair dye composition of the present invention does not cause deterioration in the feeling due to hair dying, while maintaining its dying effect.

<Unpleasant Odor Upon Mixing the Agents>

An amount of ammonia released in a certain time period upon mixing of a first-part agent and a second-part agent was compared between the compositions of Example 1 and Comparative example 1; the compositions of Example 4 and Comparative example 2; and the compositions of Example 7 and Comparative example 3. A first-part agent and a second-part agent were mixed at a ratio of 1:2, and immediately thereafter 5 g of the mixed agent was weighed out and placed in a 2.5 L beaker, and it was sealed airtight with a plastic film. One minute later, the concentration of ammonia in the beaker was measured with an ammonia detector and a gas measuring instrument (GASTEC Corporation). An amount of ammonia stripped was measured after the mixed agent was left to stand for one minute, and also after the mixed agent was magnetically stirred for one minute. The result is shown in Table 8.

TABLE 8

(Amount of ammonia stripped)

| | Concentration of ammonia (ppm) | |
|---|---|---|
| Fist-part agent | Left to stand | Stirred |
| Example 1 | 90 | 340 |
| Comparative example 1 | 120 | 400 |
| Example 4 | 80 | 320 |
| Comparative example 2 | 100 | 390 |

TABLE 8-continued (Amount of ammonia stripped)

| | Concentration of ammonia (ppm) | |
|---|---|---|
| Fist-part agent | Left to stand | Stirred |
| Example 7 | 90 | 340 |
| Comparative example 3 | 120 | 400 |

In comparison with Comparative example 1, an amount of ammonia stripped was suppressed in Example 1 by 30 ppm when left to stand, and by 60 ppm when stirred; in comparison with Comparative example 2, an amount of ammonia stripped was suppressed in Example 4 by 20 ppm when left to stand, and by 70 ppm when stirred; and in comparison with Comparative example 3, an amount of ammonia stripped was suppressed in Example 7 by 30 ppm when left to stand, and by 60 ppm when stirred.

Regarding the olfactory sensing in a human, an amount of the causative substance of a stripping odor which is present in the nose at a moment is more important than the total amount of stripping of the causative substance of an odor. For this, an organoleptic evaluation reflects the characteristic of an odor better than the quantitative measurement using a measuring instrument. In view of the above, a comparative organoleptic evaluation was conducted by 25 panelists with respect to the intensity of an unpleasant odor of Example 1 and Comparative example 1, and more than half of the panelists evaluated that the unpleasant odor of ammonia upon mixing was suppressed in Example 1.

Unpleasant odor was weaker in Example 1 15 panelists
Unpleasant odor was equal between Example 1 and Comparative example 1 6 panelists
Unpleasant odor was weaker in Comparative example 1 4 panelists <Mode of Application as a Three-Part Agent>

With 1 weight Part of a first-part agent shown in Table 1-4, 1 weight part of a second-part agent shown in Table 5 and 0.3-1 weight part of a third-part agent shown in Table 6 were mixed, and applied to goat hair at 30° C. After allowing it to act on the hair for 30 minutes, the hair was washed with an ordinary shampoo and then dried.

As a result of observation of the hue of the dyed hair, it was found that both dying effect and shampoo robustness were favorable in every sample.

The invention claimed is:

1. A hair dye composition which is provided by mixing at least a first-part agent comprising an alkaline agent and a second-part agent comprising an oxidizing agent upon application, the composition comprising, after mixing, components (a) to (c) and optionally an oxidative dye (d), wherein the pH after mixing is from 8 to 12 and the content of component (a) is from 0.1 to 20%, by weight of the hair dye composition:

(a) a betaine compound represented by formula (1) and an acid-addition salt thereof:

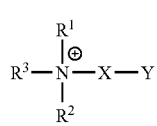

(1)

wherein $R^1$, $R^2$ and $R^3$ are the same or different from one another and each represents a $C_{1-3}$ alkyl group, X represents a $C_{1-3}$ alkylene group, Y represents $CO_2^-$, $SO_3^-$, $OSO_3^-$ and $OPO_3^-$;

(b) an oxidizing agent; and
(c) an ammonia or a salt thereof.

2. The hair dye composition according to claim 1, further comprising a cationic polymer.

3. The hair dye composition according to claim 1, further comprising at least one silicone.

4. A method for dying hair, comprising mixing a first-part agent and a second-part agent of the hair dye composition according to claim 1 right before use; applying the mixture to the hair; and washing the mixture off after letting it stand for a predetermined time.

5. The hair dye composition according to claim 1, wherein the oxidative dye (d) is present.

6. The hair dye composition according to claim 1, wherein a third-part agent, which is a powdery oxidizing agent, is present.

7. The hair dye composition according to claim 1, wherein said first-part agent has a pH of 8-12 before mixing and said second-part agent has a pH of 2-5 before mixing.

8. The hair dye composition according to claim 1, wherein component (a) is contained in either one or both of said first-part agent and said second-part agent.

9. The hair dye composition according to claim 1, wherein said component (a) is a glycine betaine represented by the following formula (2):

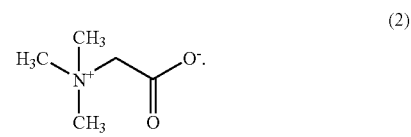

(2)

10. The hair dye composition according to claim 1, wherein component (a) is present in an amount of 0.05-5 wt % in the hair dye composition.

11. The hair dye composition according to claim 1, wherein component (b) is present in an amount of 1-6 wt % in the hair dye composition.

12. The hair dye composition according to claim 1, wherein component (c) is present in an amount of 0.2-5 wt % in the hair dye composition.

13. The hair dye composition according to claim 1, wherein a monoethanol amine or salt thereof is present as an alkaline agent in addition to component (c).

14. The hair dye composition according to claim 13, wherein the sum of the content (X), which represents the content of ammonia or salt thereof converted to ammonia in the hair dye composition, and the content (Y) which represents the content of monoethanol amine or a salt thereof as converted to monoethanol amine is 0.2-5 wt % in the hair dye composition.

15. The hair dye composition according to claim 14, wherein X/Y is 0.05:1-0.5:1.

16. The hair dye composition according to claim 1, wherein said oxidative dye (d) is not present.

17. The hair dye composition according to claim 2, wherein the cationic polymer is a copolymer of a diallyl quaternary ammonium salt, the skeletal structure of which is represented by the following formula (20) or (21):

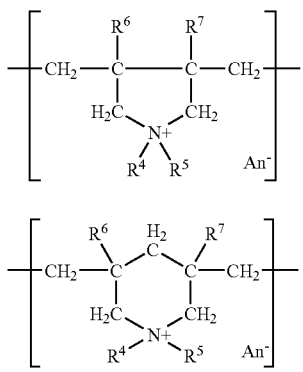

(20)

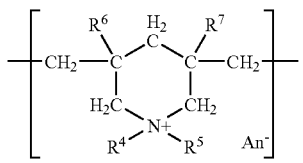

(21)

wherein $R^4$ and $R^5$ are the same or different from one another and each represents a hydrogen atom, a $C_{1-18}$ alkyl group, an aryl group, a hydroxyalkyl group, an amidoalkyl group, a cyanoalkyl group, an alkoxyalkyl group or a carboalkoxyalkyl group; $R^6$ and $R^7$ are the same or different from one another and each represents a hydrogen atom, a $C_{1-3}$ alkyl group or phenyl group; and An⁻ represents an anion.

18. The hair dye composition according to claim 3, wherein the silicone is at least one of a polysiloxane and an amino-modified silicone.

19. The hair dye composition according to claim 18, wherein the dimethylsiloxane and amino-modified silicone are both present.

20. The hair dye composition according to claim 3, wherein the total content of silicones is 0.2-15 wt % in the hair dye composition.

* * * * *